United States Patent [19]

Greenberg

[11] 4,096,284
[45] Jun. 20, 1978

[54] FLAVORING WITH α-MERCAPTOACETOPHENONE AND DERIVATIVES

[75] Inventor: Michael J. Greenberg, Chicago, Ill.

[73] Assignee: The Quaker Oats Company, Chicago, Ill.

[21] Appl. No.: 805,896

[22] Filed: Jun. 13, 1977

[51] Int. Cl.² ............................................. A23L 1/231
[52] U.S. Cl. .................................................... 426/535
[58] Field of Search ........................................ 426/535

[56] References Cited

U.S. PATENT DOCUMENTS

| | | | |
|---|---|---|---|
| 3,677,772 | 7/1972 | Mussinan et al. | 426/535 |
| 3,773,524 | 11/1973 | Katz et al. | 426/535 |
| 3,943,260 | 3/1976 | Winter et al. | 426/535 |

OTHER PUBLICATIONS

Fenaroli's Handbook of Flavor Ingredients, Furia et al. Second Ed., 1975, vol. 2, CRC Press, Inc., Cleveland, p. 7.

Arctander, Perfume and Flavor Chemicals, vol. I, 1969, Publ. by the author; Montclair, N. J., Items No. 24–26.

*Primary Examiner*—Joseph M. Golian
*Attorney, Agent, or Firm*—Mathew R. P. Perrone, Jr.

[57] ABSTRACT

Flavors in foods are enhanced by adding to the food an α-Mercaptoacetophenone and derivatives thereof. These flavorants may impart meat-like flavor to meatless compositions or augment meat flavor in meat-containing foods.

12 Claims, No Drawings

FLAVORING WITH α-MERCAPTOACETOPHENONE AND DERIVATIVES

BACKGROUND OF THE INVENTION

This invention relates to foods; and more particularly to flavored foods, and specifically pet foods, having added thereto α-Mercaptoacetophenone or derivatives thereof for the purpose of providing a meat flavor to a meatless food, or augmenting the meat flavor of a meat-containing food.

The consumption of food involves many complex factors. Consumption is always affected by supply. Further complicating the food supply is that food must not only be edible, it must also be acceptable to the consumer. This acceptability to the consumer involves many complex factors. Added to these factors are the complications of custom and national tradition that distinguish and interfere with the consumption of otherwise edible material. In other words, not only is the food supply short, some of the food which is available, nutritional and edible is still unacceptable. This unacceptability is due in part, to the organoleptic property of the food known as flavor. Flavor is basically associated with the taste, aroma, appearance, and texture of foodstuffs. The taste and aroma aspect of a flavorant are major variables in determining the acceptability of a foodstuff.

Much research time, skill, and money are devoted to the development of suitable flavors which can then be used to render acceptable those edible materials or foods which are otherwise unacceptable. Flavorants can render foods more acceptable from both a taste and aroma standpoint. Additionally, flavorants can help a particular food maintain its natural aroma and avoid flavor deterioration. These advantages for flavorants justify the time spent in determining suitable flavorants.

Flavorants have contrasting requirements of thermal stability and volatility. Aroma stability is required so that both the aroma and desired taste will remain with the food for a sufficient time to achieve the desired effect of making the food more acceptable. Volatility is required so that the aroma of the flavorant will in some way indicate its presence in the food and perform the desired function of making it more acceptable to the consumer. However, the more volatile a flavorant is, the shorter period of time it will provide the pleasing aroma. On the other hand, the more thermally stable a flavorant is, the less volatile it becomes and more is required to give a pleasing aroma. These contrasting desirable features must be balanced in order to achieve an effective flavorant.

In addition to having the desired volatility and long term thermal stability, the flavorant must also be capable of surviving hydrolytic conditions and strenuous food processing conditions. These conditions can be extremely strenuous and have an adverse affect on a compound which must be volatile. Thus, the incorporation of this desired flavorant into a food may cause problems in the formulation of a food containing the flavorant.

Food as used herein is well defined in the prior art. U.S. Pat. No. 3,876,809 to Mussinan et al. (incorporated herein by reference) clearly defines food and the purposes thereof. Flavorants provide organoleptic acceptability for foods. Since meat is a most acceptable form of protein food, it is extremely desirable to provide both the taste and aroma of meat to be added to protein containing foods. In this fashion, protein containing foods not having a meat flavor may be made more acceptable to the consumer.

These flavorant compounds provide meat-like flavor for meatless edible compositions and also augment the existing meat flavor in meat containing foods. In this fashion, these compounds are suitable as flavorants. Foods containing no meat, but which are nutritionally equivalent to meat, can be made more acceptable by including such flavorants therein to provide the aroma and taste flavor of meat in addition to the appearance and nutrition desired. Where meats are used, the flavorant can maintain or augment the meat aroma and taste to thereby provide wider use of otherwise unusable meat portions. In this fashion, the flavorants can render more acceptable otherwise unacceptable or acceptable — but not preferred products.

A major problen with the use of aliphatic α-mercaptoketones as flavorants is that they are usually volatile due to relatively low molecular weight. This volatility means that the compounds are not stable to the amount of heat used in food processing to a sufficient extent to survive the heat processing conditions. However, the desirable flavor makes it useful to have such compounds in the product. If it were possible to stabilize the mercaptoketone compound while maintaining the desired flavoring characteristics, a highly suitable result can be obtained. By replacing an alkyl group with an aromatic phenyl group, improved stability may be achieved, because the larger aromatic molecules are less volatile than the alkyl group.

SUMMARY OF THE INVENTION

Therefore, an object of this invention is to improve the flavor of food.

A further object of this invention is to provide a food having a stable flavor.

Yet another object of this invention is to provide a food having a flavorant with sufficient volatility.

Still another object of this invention is to provide a flavorant capable of surviving food processing conditions.

A further object of this invention is to provide a food having its flavor increased.

A still further object of this invention is to provide a food having a meaty aroma and taste.

These and other objects of this invention are achieved by adding to the food an α-Mercaptoacetophenone or derivatives thereof to serve as a flavorant and thereby vary, fortify, modify, enhance, or improve the flavor and aroma of a foodstuff.

DESCRIPTION OF THE PREFERRED EMBODIMENTS

A meat flavor or aroma is imparted to foods by addition thereto of an α-Mercaptoacetophenone (a) or a derivative thereof (b) having the formulas indicated:

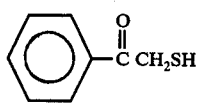　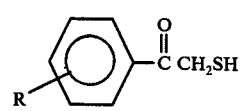

(a)　　　　　　　　　(b)

The compounds above-referenced when added to a food provide a meat-like taste and aroma for the food when taken singly or in any combination. These compounds either provide meat flavor for food, augment meat flavor for food, or mask otherwise unacceptable flavoring for a food. These compounds or mixtures thereof are customarily used in an amount effective to impart the desired aroma or flavor to the food. More specifically, up to about 2 percent by weight of the food comprises the compounds set forth. Even more specifically, about 0.0001 percent to about 1 percent by weight of the food comprise these compounds. Most preferably, these compounds comprise about 1 ppm to about 100 ppm by weight of the food. In this fashion, the most desirable flavor is imparted to the food.

The substituents indicated on the formula permit R to be an alkyl group containing 1–4 carbon atoms, hydrogen, a hydroxyl group, alkoxy group containing 1–4 carbon atoms, an acetyl group, a phenacyl group, a benzyl group, a halogen, or mixtures thereof. Especially preferred halogens are chlorine and fluorine.

The compounds described in this application may be used singly or in admixtures comprising two or more thereof. The formulation may combine additional flavoring materials such as furfural, benzaldehyde, and hexanal to simulate a wide variety of organoleptic characteristics. In addition, its derivatives may be admixed with one or more flavorant adjuvants such as stabilizers, thickeners, surface active agents, conditioners, flavorants and flavor intensifiers to provide suitable flavor imitative of roasted meats of various types.

The compounds described in this application can be added to the foods to be flavored by any conventional techniques. Typical conventional techniques include spray drying, blending, stirring, dissolving and the like. The addition of these compounds is carried out in any stage of the preparation of the foodstuff to which the compounds are to be applied. These compounds may be added before, after or during processing of canned, semi-moist or dry pet food. For example, if the product is formed by extrusion, the flavor may be added to the dough before extrusion, injected into the extruder or sprayed on the product as it leaves the extruder.

These flavorants can be added to almost any type of food, but are particularly applicable to pet foods of the moist, semi-moist or dry type. Typical pet foods which may use the particular flavorants are disclosed in U.S. Pat. No. 3,922,353 to Bernotavicz, U.S. Pat. No. 3,380,832 to Bone, U.S. Pat. No. 3,738,847 to Bechtel, U.S. Pat. No. 3,883,672 to Bone and Shannon, U.S. Pat. No. 3,974,296 to Burkwall, and U.S. Pat. No. 3,984,576 to Burkwall, Leyh, and Reagan. The referenced patents are incorporated herein by reference.

The means of making these α-Mercaptoketones are well known in the art as evidenced by *Chemical Abstracts*, Volume 72, 1970, No. 55006Y and *Chemical Abstracts*, Volume 79, 1973, No. 66020U. In the *Chemical Abstracts* Volume 72, is the abstract of the Japanese Patent Aromatic mercaptomethyl ketones by Minakami. In *Chemical Abstracts* Volume 79 is the abstract of the article by Pavlova.

Even though the concept of this invention can be readily understood from the above description by one having ordinary skill in the art, the following examples are presented to guarantee a complete understanding of the invention without limiting the invention. All parts and percentages are here and throughout the specification are by weight unless otherwise specified. By up to here and throughout the specification is meant at least a trace of the component is present for a lower limit.

EXAMPLE I

This example is a synthesis of α-Mercaptoacetophenone. To a 250 ml three-necked round bottom flask equipped with mechanical stirrer, addition funnel and gas inlet tube is placed pyridine (7.5g) saturated with Hydrogen Sulfide. The solution is vigorously stirred. 2 Chloro-acetophenone (23.2g) in ether (100ml) was slowly added with vigorous stirring and hydrogen sulfide addition at room temperature over a thirty minute period. The mixture was stirred an additional 90 minutes at room temperature, then stirred for 30 minutes at 50° C., and poured into a mixture of concentrated hydrochloric acid (90g) and crushed ice (500g). The mixture is extracted with 3–50 ml portions of ether. The ether extract is dried ($Na_2SO_4$) and distilled yielding a clear colorless oil; 3.0g (13%); bp 82°(0.3mm); IR (Neat) 3050 (C—H), 2910 (C—H), 2550 (S—H), 1670 (C=O), 1593$cm^{-1}$)C=C); PMR ($CCl_4$), 2.40 ppm (t,3,S—H), 4.14 ppm (d,2,$CH_2$—S—H) and 7.50–8.43 (m,5,aromatic) clearly showing the product to be α-mercaptoacetophenone.

EXAMPLE II

The flavoring of Example I is topically applied to a commercial semi-moist pet foood (Ken-L-Ration Burger, available from The Quaker Oats Co.). Tests are conducted with dogs of varying breed and size to compare preference of the control product containing no flavorant and the same product containing α-mercaptoacetophenone of varying concentrations. The results of these tests shown below indicate excellent palatability of the product containing α-mercaptoacetophenone, and that the palatability in this case is linear with log concentration.

| Flavorant Level in parts per million | % Test Material Consumed | % Control Consumed |
|---|---|---|
| 3 | 71.3 | 28.7 |
| 5 | 75.6 | 24.4 |
| 6 | 81.4 | 18.6 |

The average percent consumed of test material for 3 ppm is 71.3% and for 5 ppm it is 75.6%. A statistically significant preference was demonstrated by the pet food flavored with α-mercaptoacetophenone at the 6 ppm level.

EXAMPLE III

Each α-mercaptoacetophenone is added to a dry commercial dog food (KLR Biskit available from The Quaker Oats Co.) rehydrated with 65% water on a weight basis significant palatability is achieved.

| Level of α-mercaptoacetophenone | % Test Material Consumed | % Control Consumed |
|---|---|---|
| 5 ppm | 62.6 | 37.4 |
| 10 ppm | 66.3 | 33.7 |

Having now fully described and dislcosed this new invention, what is claimed and sought to be secured by Letters Patent of the United States is:

1. A process for altering the flavor of a foodstuff comprising adding to the foodstuff an amount of at least one flavorant selected from the group consisting of α-mercaptoacetophenone and derivatives thereof effective to impart a meat-like flavor and represented by the formula:

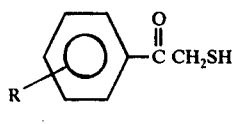

wherein R is an alkyl group containing from 1-4 carbon atoms, hydrogen, an alkoxy group containing from 1-4 carbon atoms, a hydroxyl group, an acetyl group, a phenacyl group, or a benzyl group.

2. A process as defined in claim 1 wherein the flavorant is α-mercaptoacetophenone.

3. A foodstuff comprising an amount of at least one flavorant selected from the group consisting of α-mercaptoacetophenone and derivatives thereof effective to impart a meat-like flavor and represented by a formula having a ring structure of:

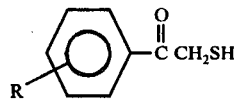

wherein R is an alkyl group of 1-4 carbon atoms, hydrogen, an alkoxy group containing from 1-4 carbon atoms, a hydroxyl group, acetyl group, phenacyl group, or benzyl group.

4. A composition as defined in claim 3 wherein the flavorant is α-mercaptoacetophenone.

5. A composition as defined in claim 3 wherein the foodstuff is a pet food.

6. The pet food of claim 5 wherein the flavorant comprises up to 2 percent by weight of the pet food.

7. The pet food of claim 6 wherein the flavorant comprises about 0.0001 to about 1 percent by weight of the pet food.

8. the pet food of claim 7 wherein the flavorant comprises about 1 to about 100 parts per million of the pet food.

9. A composition as defined in claim 3 wherein the foodstuff is a dry pet food.

10. A composition as defined in claim 3 wherein the foodstuff is a semi-moist pet food.

11. A composition as defined in claim 3 wherein the foodstuff is a canned pet food.

12. A composition as in claim 4 wherein the foodstuff is a pet food.

* * * * *